US00PP36328P2

(12) United States Plant Patent
Delabroye

(10) Patent No.: US PP36,328 P2
(45) Date of Patent: Dec. 17, 2024

(54) ***HEUCHERA* PLANT NAMED 'Spitfire'**

(50) Latin Name: ***Heuchera* hybrid**
Varietal Denomination: Spitfire

(71) Applicant: Thierry Delabroye, Hantay (FR)

(72) Inventor: Thierry Delabroye, Hantay (FR)

(73) Assignee: Delabroye Sandrine, Hantay (FR)

( * ) Notice: Subject to any disclaimer, the term of this patent is extended or adjusted under 35 U.S.C. 154(b) by 0 days.

(21) Appl. No.: 18/614,725

(22) Filed: Mar. 24, 2024

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heuchera* plant named 'Spitfire' that is characterized by its large leaves, its foliage that is green in color with veins surrounded with a dark green-black color, its evergreen foliage in U.S.D.A. Zone 6 or greater, and its vigorous growth habit.

3 Drawing Sheets

Botanical classification: *Heuchera* hybrid.
Cultivar designation: 'Spitfire'.

BACKGROUND OF THE INVENTION

The present invention relates to a new and distinct cultivar of *Heuchera* of hybrid origin, botanically known as *Heuchera* 'Spitfire' and is hereinafter referred to by its cultivar name 'Spitfire'.

'Spitfire' was derived from a controlled breeding program conducted by the Inventor in his nursery in Hantay, France. The breeding program focuses on obtaining a new cultivar of *Heuchera* with resistance in full sun and dry soil and green foliage with black veins. 'Spitfire' was selected in May of 2022 by the Inventor as a single unique plant derived from a cross made in May of 2021 between unnamed and unpatented proprietary plants from his breeding program.

Asexual propagation of the new cultivar was first accomplished under the direction of the Inventor by tissue culture using meristematic tissue in Rijswijk, The Netherlands in May of 2022. Asexual propagation of the new cultivar by meristem tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Spitfire' as a unique cultivar of *Heuchera*.

1. 'Spitfire' exhibits large leaves.
2. 'Spitfire' exhibits foliage that is green in color with veins surrounded with a dark green-black color.
3. 'Spitfire' exhibits evergreen foliage in U.S.D.A. Zone 6 or greater.
4. 'Spitfire' exhibits a vigorous growth habit.

Both of the parent plants of 'Spitfire' differ from 'Spitfire' in having lighter green leaves that are smaller in size.

'Spitfire' can be most closely compared to an unnamed plant of *Heuchera villosa* ssp. *macrorhiza* (not patented) and *Heuchera* 'Beauty Color' (not patented). an unnamed plant of *Heuchera villosa* ssp. *macrorhiza* is similar to 'Spitfire' in having a large plant size, large leaves, and resistance to dry soil. an unnamed plant of *Heuchera villosa* ssp. *macrorhiza* differs from 'Spitfire' in having light green foliage that is less curly with lighter purple veins, a slightly smaller leaf size, and a less vigorous plant habit. *Heuchera* 'Beauty Color' is similar to 'Spitfire' in having green foliage with dark colored veins. *Heuchera* 'Beauty Color' differs from 'Spitfire' in having a slightly smaller leaf size, a shorter plant height, and foliage that is less curly, less rounded in shape and that have a silver overlay.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listings by Vitro Westland.

BRIEF DESCRIPTION OF THE DRAWINGS

The accompanying color photographs illustrate the overall appearance and distinct characteristics of the new *Heuchera*. The photographs were taken of an 18-month-old plant as grown in a greenhouse in a 19-cm container in Hantay, France.

The photograph in FIG. 1 provides a side view of the plant of 'Spitfire' in bloom.

Figure 1:
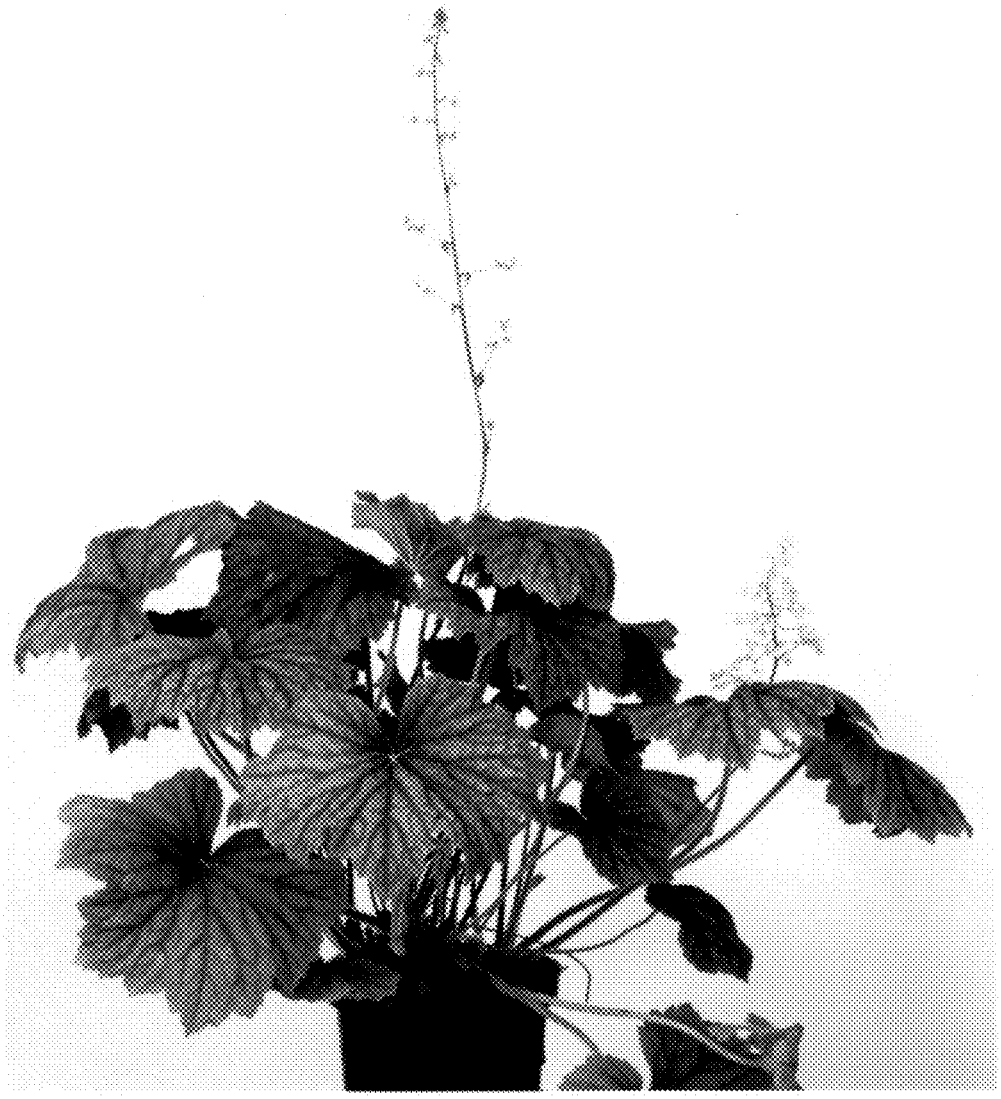
Figure 2:
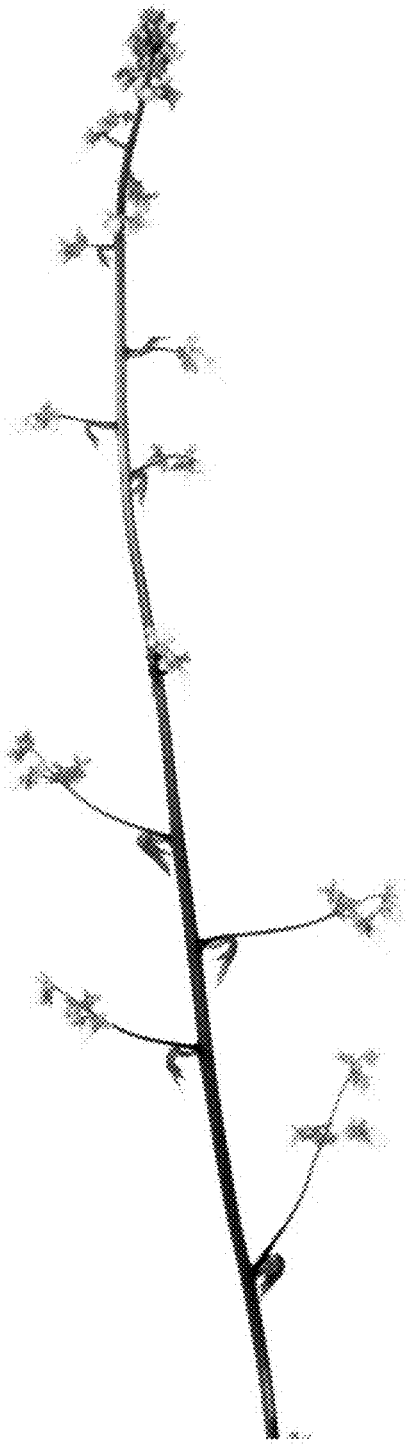

The photograph in FIG. 2 provides a close up of the inflorescence of 'Spitfire'.

Figure 3:
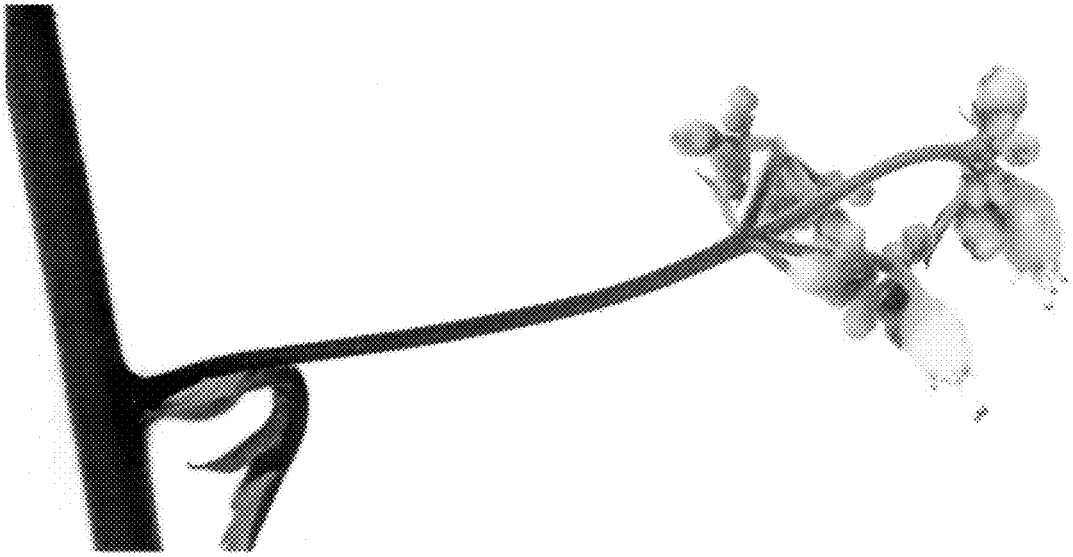

The photograph in FIG. 3 provides a close up of the flowers of 'Spitfire'.

Figure 4:
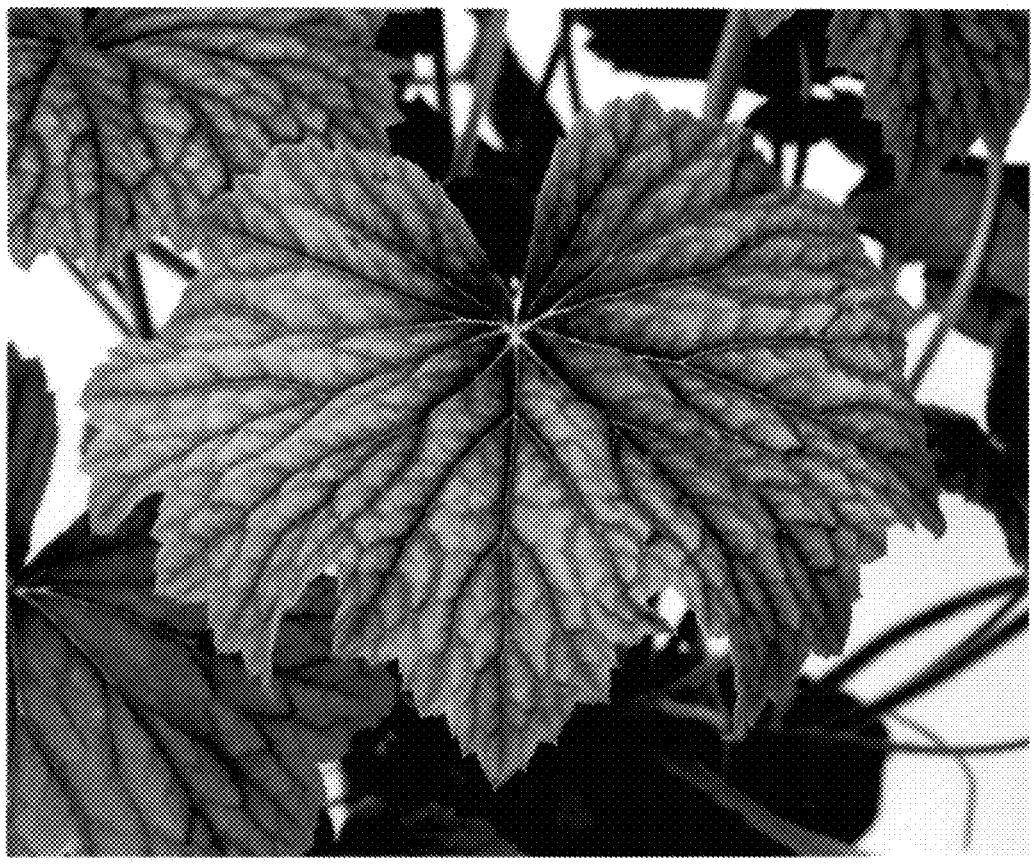

The photograph in FIG. 4 provides a close up of a leaf of 'Spitfire'.

The colors in the photographs are as close as possible with the photographic and printing technology utilized and the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown in a greenhouse in 19-cm containers in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to November in France.

*Plant type*.—Herbaceous perennial, evergreen in U.S.D.A. Zone 6 or greater.

*Plant habit*.—Open-mounded with inflorescences held above the foliage.

*Height and spread*.—An average of 46 cm in height to top of foliage (85.4 cm to top of inflorescence) and 69 cm in width as an 18-month-old plant grown in a container.

*Hardiness*.—At least in U.S.D.A. Zones 4 to 9.

*Diseases and pests*.—Good resistance has been observed to powdery mildew (most likely caused by *Podosphaera* spp.), no susceptibility or resistance to pests has been observed.

*Root description*.—Fibrous roots on woody rootstalks, 158D in color.

*Propagation*.—Tissue culture.

*Time required for root development*.—An average of 3 weeks for root initiation, 6 weeks to produce a young plant.

*Growth rate*.—Vigorous.

Stem description (peduncle, flowering stem):

*Shape*.—Round.

*Stem color*.—A blend of 143A and 144A, proximal end tinged 177B.

*Stem size*.—An average of 4 mm in diameter and 77 cm in length.

*Stem strength*.—Moderately strong.

*Stem aspect*.—Flowering stems grow at an angle of 60° to 75° (0°=horizontal).

*Stem surface*.—Slightly glossy, densely covered with short hairs; an average of 0.5 mm in length, NN155D.

*Branching habit*.—Flowering stems emerge from basal rosette, average of 4 basal rosettes.

Foliage description:

*Leaf shape*.—Orbicular to reniform in outline, slightly convex.

*Leaf division*.—Simple.

*Leaf base*.—Hastate, lobes free.

*Leaf apex*.—Short abruptly acute.

*Leaf venation*.—Laciniate, mature upper surface 150A, mature lower surface a blend of 144A and 145B.

*Leaf margins*.—Crenate with abruptly acute tips on each tooth, slightly to moderately coarsely undulate.

*Leaf attachment*.—Petiolate.

*Leaf arrangement*.—Alternate in basal rosettes.

*Leaf lobes*.—Lobed, average number of lobes: 7 to 9, occasionally 11.

*Leaf orientation*.—Typically nearly horizontal to petiole and slightly cupped.

*Leaf surface*.—Upper surface; matte, non-rugose, moderately covered with very short hairs, an average of 0.75 mm in length, transparent and too sparse to measure color, lower surface; matte, non-rugose, margins densely covered with very short strigose hairs; an average of 1 mm in length, transparent and 156D in color.

*Leaf color*.—Young upper surface; N144C, veins a blend of 175A and 178A, young lower surface; 144B, main vein 146D, secondary veins 176C, mature upper surface; 144A and N144C, then turning to 137A, area around veins tinged with a blend of 197A, N199A, and 200B, veins 150A, mature lower surface; 144B, then turning to 138B, area around veins 197B to 197C, veins 144A and 145B.

*Leaf size*.—An average of 20.2 cm in length and 22.9 cm in width.

*Leaf quantity*.—An average of 20 per plant.

*Petioles*.—An average of 32.1 cm in length, 6 mm in diameter, upper surface color; 146B, slightly tinged at the proximal end with 177B, lower surface color; 144A, slightly tinged at the proximal end with 177B, both surfaces are slightly glossy, moderate in strength, densely covered with very short hairs; an average of 0.2 mm in length, transparent and NN155A in color.

*Stipules*.—At the base of each leaf, acute apex, an average of 2.3 cm in length and 7 mm in width, surface similar to leaf, color; 144A, center 185C to 185D.

Flower description:

*Inflorescence type*.—Numerous small bell-shaped flowers arranged on panicles on peduncles emerging from a basal rosette.

*Inflorescence size*.—An average of 38.8 cm in height and 10.1 cm in diameter.

*Inflorescence number*.—An average of 2 per plant.

*Flower fragrance*.—None.

*Flower quantity*.—Average of 400 buds and flowers per inflorescence.

*Flower lastingness*.—Average of one week.

*Flower buds*.—Ovate in shape, an average of 0.3 mm in diameter and 0.2 mm in diameter, matte surface, densely covered with very short glandular hairs; an average of 0.3 mm in length and too small to measure color, color; 158C to 158D, lower half 145B.

*Flower aspect*.—Upright, outwardly and nodding.

*Flower type*.—Single, campanulate.

*Flower size*.—Average of 7 mm in length (depth) and 4.5 mm in diameter.

*Petals*.—5, rotate arrangement and implanted in the hypanthium at base, 1 whorl, narrow elliptic in shape, margin is entire, apex is narrowly acute, base is narrow acuminate, an average of 3 mm in length and 6 mm in width, both surfaces matte and glabrous, color; when opening, and fully opened upper and lower surface NN155D.

*Calyx*.—Campanulate, 4.5 mm in length, 3 mm in diameter.

*Sepals*.—An average of 5, lower 50% fused into campanulate hypanthium, free part short oblong in shape, an average of 4.5 mm in length and 1 mm in width, margin is entire and fused into hypanthium, apex is obtuse, fused base, color; when opening upper surface 157D, lower half 145C, when opening lower surface 158C to 158D, lower half 145B, fully open upper surface N155B, lower half 150D, fully open lower surface NN155B, top tinged 145A, lower half 145D, both surfaces are matte, upper surface glabrous, lower surface is densely covered with very short glandular hairs; an average of 0.4 mm in length and too small to measure color.

*Pedicels*.—An average of 1 mm in length and 0.5 mm in diameter, primary flower aspect straight on top of secondary pedicel, secondary and tertiary flower aspect is 35°, color; a blend of 144B and 144C, moderate in strength, surface matte and densely covered with very short soft glandular hairs; average of 0.3 mm in length and too small to measure color.

Reproductive organs:

*Gynoecium*.—Pistils; 2, occasionally 3, 4.75 mm in length, stigma; club-shaped, 155A in color, 0.2 mm in diameter, style; an average of 4.5 mm in length and N155B in color, ovary; 145C in color.

*Androecium*.—Stamens; 5, anthers; ovate in shape, 0.5 mm in length, N172C in color, filament; 3 mm in length, NN155D in color, pollen; low in quantity, too little to measure color.

*Seed fruit*.—No fruit or seeds were observed to date.

It is claimed:

1. A new and distinct cultivar of *Heuchera* plant named 'Spitfire' as herein illustrated and described.

* * * * *